United States Patent
Dukhin et al.

[11] Patent Number: 6,109,098
[45] Date of Patent: Aug. 29, 2000

[54] PARTICLE SIZE DISTRIBUTION AND ZETA POTENTIAL USING ACOUSTIC AND ELECTROACOUSTIC SPECTROSCOPY

[75] Inventors: Andrei Dukhin, Goldens Bridge; Philip Goetz, Katonah, both of N.Y.

[73] Assignee: Doukhin Dispersion Technology, Inc., Mount Kisco, N.Y.

[21] Appl. No.: 09/108,072

[22] Filed: Jun. 30, 1998

[51] Int. Cl.[7] .......................... G01N 29/00; G01N 15/00; G01N 27/00; C21B 7/24; G01R 29/12

[52] U.S. Cl. .......................... 73/64.42; 73/865.5; 73/584; 324/71.1; 324/457

[58] Field of Search .............................. 73/64.42, 61.75, 73/587, 64.48, 53.01, 606, 64.53, 61.41, 584, 865.5; 324/71.1, 705, 457, 453, 452, 709, 713; 399/27

[56] References Cited

U.S. PATENT DOCUMENTS

| | | | |
|---|---|---|---|
| 4,497,208 | 2/1985 | Oja et al. | 73/584 |
| 4,907,453 | 3/1990 | Marlow et al. | 73/584 |
| 5,059,909 | 10/1991 | O'Brien | 324/457 |
| 5,121,629 | 6/1992 | Alba | 73/61.41 |
| 5,245,290 | 9/1993 | Cannon et al. | 324/457 |
| 5,293,773 | 3/1994 | Babchin et al. | 73/64.48 |
| 5,294,891 | 3/1994 | Saklikar et al. | 324/705 |
| 5,528,133 | 6/1996 | Saklikar | 324/71.1 |
| 5,616,872 | 4/1997 | O'Brien | 73/865.5 |
| 5,831,150 | 11/1998 | Sowerby et al. | 73/61.75 |

*Primary Examiner*—Hezron Williams
*Assistant Examiner*—Jay L. Politzer

[57] ABSTRACT

A device is described which combines Acoustic and Electroacoustic spectrometers to characterize both particle size distribution and zeta potential for concentrated dispersed systems.

The Acoustic Spectrometer measures both attenuation and sound speed for multiple frequencies using each measurement to help optimize and correct the other. The attenuation spectra is used to calculate particle size.

The Electroacoustic Spectrometer measures Colloid Vibration Current (CVI), correcting the measured value using attenuation and sound speed data from the Acoustic Spectrometer. The Colloid Vibration Current is used to calculate zeta potential taking into account the particle size calculated from the acoustic measurement as well as particle interaction.

Sound speed and multiple frequency CVI measurement provide additional experimental data to check the validity of the data.

11 Claims, 4 Drawing Sheets

Fig.4
alumina
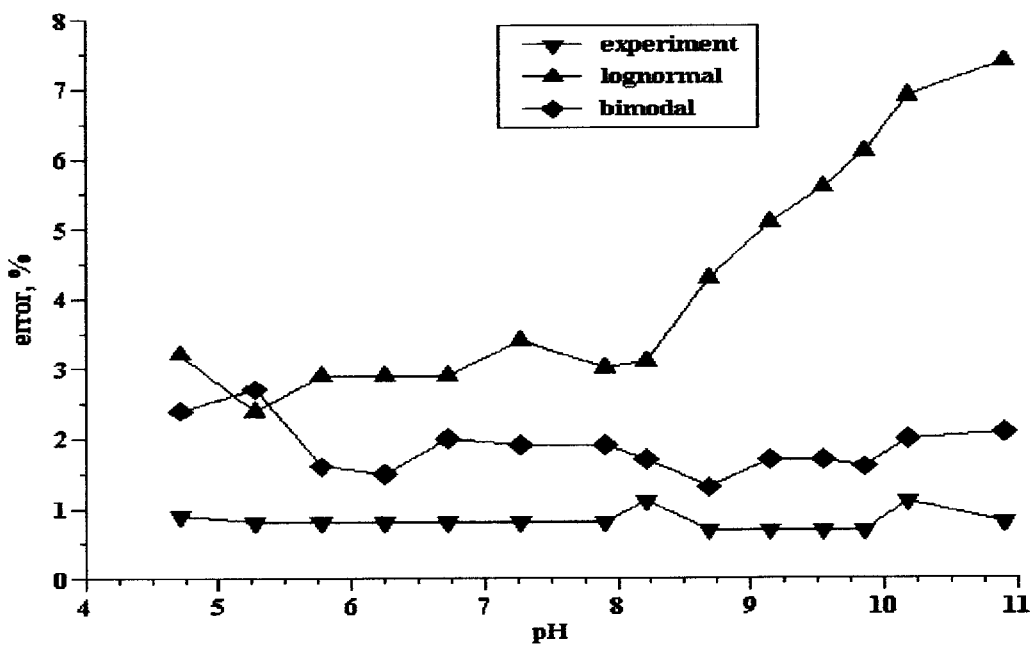
rutile
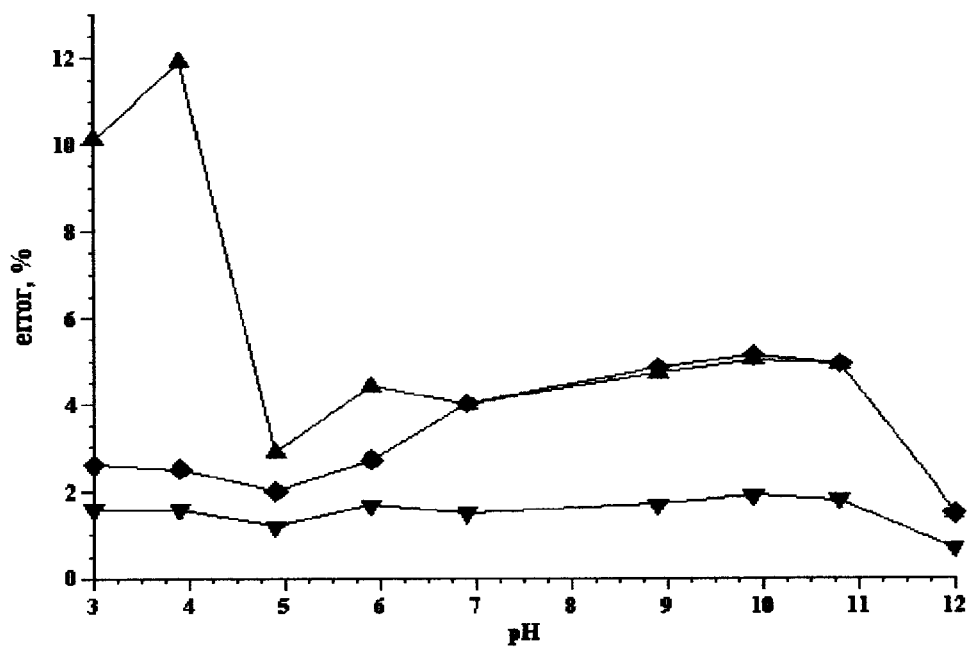

PARTICLE SIZE DISTRIBUTION AND ZETA POTENTIAL USING ACOUSTIC AND ELECTROACOUSTIC SPECTROSCOPY

BACKGROUND OF THE INVENTION

The present invention is directed to a particular kind of dispersed system that can be described as a collection of particles immersed in a liquid. The particles can be either solid (suspension) or liquid (emulsions). This kind of dispersed system plays an important role in all kind of paints, lattices, food products, cements, minerals, ceramics, blood etc.

These systems have a common feature. They all have a very high surface area because of the small particle size. Therefore surface related phenomena determine their behavior in various processes. This patent deals with dispersed systems where these surface effects are dominant, corresponding to a range of particle size up to about 10 microns.

Characterization of suspensions and emulsions is important for the manufacture as well as the design of new systems with improved properties. There are two basic notions for characterizing these dispersed systems: "particle size distribution" and "zeta potential". There are several methods for determining these characteristics. Most methods are based on light, for example: microelectrophoresis; light scattering; light diffraction; etc. There is a new alternative method based on ultrasound which is rapidly becoming important. The ultrasound method has a large advantage over traditional light based techniques because it is able to characterize a concentrated systems without dilution. Light based methods usually require extreme dilution in order to make the sample sufficiently transparent for measurement.

The present invention is directed to an improved device and method of using the ultrasound characterization technique.

BACKGROUND ART

There are two methods for ultrasound characterization of disperse systems: Acoustics and Electroacoustics. In both methods, the interaction of sound with the dispersed particles provides useful information. An acoustic method applies an acoustic input and measures an acoustic response. An electroacoustic method applies an acoustic input and measures an electrical response, or conversely applies an electrical input and measures an acoustic response.

Both methods are macroscopic, in the sense that they include two steps. The first step is to perform some experiment on the disperse system to obtain a set of measured properties related to certain macroscopic qualities such as temperature, pH, attenuation, sound speed, etc. The second step is an analysis of the measured data to compute the desired characteristics such as particle size or zeta potential from these measured properties. This analysis requires three tools: a model dispersion, a prediction theory, and an analysis engine.

A dispersion model is an attempt to describe the real world dispersion in terms of a set of model parameters including, of course, the desired characteristics. The model, in effect, makes a set of assumptions about the real world in order to simplify the complexity of the dispersion and thereby also simplify the task of developing a suitable prediction theory. For example, most particle size measuring instruments make the assumption that the particles are spherical and therefore a complete geometrical description of the particle is given by a single parameter, its diameter. Obviously such a model would not adequately describe a dispersion of carpet fibers which have a high aspect ratio and any theory based on this over-simplified model might well give incorrect results. The model dispersion may also attempt to limit the complexity of the particle size distribution by assuming that it can be described by certain conventional distribution function such as for example a log-normal distribution.

A prediction theory describes some of the measured properties in terms of the model dispersion. A prediction theory for Acoustic Spectroscopy would attempt to describe the attenuation and sound speed in terms of the model parameters. Similarly, a prediction theory for electroacoustics would attempt to describe some electroacoustic measurement in terms of the model dispersion.

An Analysis Engine is essentially a set of algorithms implemented in a computer program which calculates the desired characteristics from the measured data using the knowledge contained in the prediction theory. The analysis can be thought of as the opposite or inverse of prediction. Prediction describes some of the measured properties in terms of the model dispersion. Analysis, given only the values for some of the model parameters, attempts to calculate the remaining properties by an analysis of the measured data. There are many well-documented approaches to this analysis task and that are known to those of ordinary skill in the art.

The prior art related to the design of hardware for collecting the measured properties of the dispersion (attenuation, sound speed, CVI, etc.) and the related prediction theory for calculating these measured properties from the model parameters are described below. Since the hardware, measured properties, and prediction theory for calculating particle size and ζ potential are quite different for Acoustics and Electroacoustics, the background art for these two methods are described separately.

ACOUSTICS Background

Acoustics deals with the measurement of sound attenuation and sound speed. As is known to those of ordinary skill in the art, there are many different approaches to measure these parameters in dispersed systems. However, only two approaches are devoted to small particles below 10 microns have been commercialized and are explained herein.

First Acoustic Hardware Approach

The first approach suitable for small particles was suggested by Pellam and Galt from MIT in 1946. There are two pertinent features of this approach: the use of a pulse technique and a variable gap between the transducer and receiver of the ultrasound pulse. The first implementation of this approach measured both sound speed and attenuation, however, at only one frequency. Later, this approach was modified and commercialized for measuring just attenuation but over a wide frequency range from 1 to 100 MHz.

The variable gap feature provides a much wider dynamic range of sound attenuation measurement than can be provided by a fixed gap device. The sensor loss is measured as a function of the gap between transmitting and receiving transducers. This loss, expressed in decibels (dB), should be a linear function of the gap. A linear regression analysis of the sensor loss gives the colloid attenuation in decibels per centimeter (dB/cm) which is an intensive property of the dispersed system. This variable gap technique is a very important feature of this approach because the attenuation of the real dispersed systems varies over a wide range from 0.1 dB/cm for water at low frequency to 1000 dB/cm for curing cement at 100 MHz.

This first approach has many advantages over the yet to be described second method. The pulse technique eliminates problems related to reflection and errors due to standing waves in a continuous wave system. The signal-to-noise ratio can be improved almost indefinitely by collecting more and more pulses. The approach does not require any calibration with known dispersed system.

Nevertheless, this first approach requires some improvement when it is applied to real world concentrated systems. Although this approach initially envisioned both attenuation and sound speed measurement, the sound speed part has never been developed as part of an integrated instrument. The lack of sound speed data sometimes causes an artificial excess attenuation at low frequency. Correct sound speed information is necessary in order to sample the received sound pulse at the correct moment in time. With inaccurate sound speed information, the timing errors accumulate at progressively larger gaps, causing the pulse to be sampled at not quite the peak value for larger gaps, which in turn causes an apparent excess attenuation. For low frequencies, the attenuation is often small to begin with, requiring measurements over the available gap range. Small errors in sound speed information can cause significant timing errors for the larger gaps. In contrast, the attenuation at high frequency is typically large to begin with, restricting the use of the larger gaps, and the timing errors due to sound speed uncertainties are less significant. Any excess attenuation at low frequency can cause error in the calculated particle size distribution. It is clear that sound speed measurements greatly enhances the quality of the technique. Although sound speed measurement of samples with low attenuation is relatively conventional, highly attenuating concentrated samples require a novel approach of the present invention.

Attenuation of sound is associated with the change of the sound speed relative to the frequency. It happens in so-called dispersive medium. For such a system, where the sound speed is a function of frequency, we must be careful to distinguish between three different wave velocities: the phase sound speed, the group sound speed, and the signal sound speed.

The phase sound speed $c_\phi$ is the speed with which the phase angle of a simple harmonic wave progresses with distance. The group sound speed is the speed for the progress of the "center of gravity" of a group of waves that differ somewhat in frequency. The speed of surfaces of constant phase angle in this group wave is defined as $c_a$ and is equal to the phase speed of the component of average frequency. For a pulse, the speed of the point of maximum peak amplitude, the point where the various signal component are all in phase, is not $c_a$ but $c_g$.

If the phase speed is independent of frequency, then the group speed is equal to the phase speed. However, if the center frequency of the pulse is at a point of significant dispersion then the group speed describing the propagation of the peak amplitude of the pulse will be quite different than the phase speed.

Finally there is the signal speed which is the velocity of the front of a group of waves, the speed at which a receiver first learns that a signal has been launched from the transmitter. Since in a dispersive media some components of the pulse reach the receiver ahead of other components, the shape of the pulse can not be maintained.

Second Acoustic Hardware Approach

This second approach is described in the U.S. Pat. No. 5,121,629 by Alba. This approach employs a continuous plane waves instead of a pulse technique. This approach also employs a variable gap, however, this feature is used for different purpose. The sensor loss is simply measured at a single gap for which the highest signal to noise ratio is obtained. No mention is made of any use of sensor loss information at different gaps, any regression of the data, or separation of colloid losses from the transducer loss.

The hardware design for the second approach is much more complex than the first. In order to cover more or less the same frequency range, the second approach apparently requires two pairs of broad band film transducers whereas the first one achieves this with a single transducer pair. The implementation of the second approach requires a sample volume of approximately 3 liters, whereas the second one requires only 100 ml samples.

Although the first approach is simpler from a hardware standpoint, it does require sophisticated software which is able to acquire a variable number of pulses in real time, perform regression and statistical analysis, and calculate the best PSD and $\zeta$ potential employing sophisticated models for both the colloid and the PSD. This software needs a high level of computer power that is now available.

Prediction Theory Related to Acoustics

As is known to those of ordinary skill in the art, calculation of particle size or other particle properties from the attenuation spectra requires an acoustic prediction theory. Such theories are made possible by creating first a model dispersion based on certain simplifying assumption. Typically it is assumed that the real dispersed system can be modeled as a collection of separate homogeneous spherical particles in a Newtonian liquid. It is also assumed that these particles can be characterized by certain properties, such as density and volume fraction. It is clear that these model assumptions are not always valid, particularly for a flocculated or structured system. Unfortunately, there is no criterion in the literature which allows one to check the validity of the model for use with a particular concentrated system. The user may be unaware and attempt to apply acoustic or electroacoustic theories to systems for which they are not valid. For example a dispersion of hollow glass spheres are clearly not homogeneous particles.

The suitability of the model dispersion is somewhat less of a problem for dilute systems since there is less likelihood of flocculation or structure although the requirements for sphericity, homogeneity, and a Newtonian media still exist. Partly for this reason, and more likely because the theory is much simpler, acoustic theory has been developed initially only for dilute dispersed systems.

However, all of these theories are valid only for dilute systems because they neglect both hydrodynamic and thermodynamic particle—particle interaction. These theories require the acoustic field for a single particle. This field is calculated assuming no influence from neighboring particles. For this reason, the application of the EKAH theory for interpreting attenuation spectra of the concentrated systems, as suggested by Alba in the U.S. Pat. No. 5,121,629 is not justified. He suggests using EKAH theory in combination with a multiple scattering approach. This is not adequate because even the multiple scattering approach requires a single particle acoustic field which is known only for a single particle in infinite media.

The EKAH theory is mathematically quite complex and there is no way to generalize it for a concentrated system. Fortunately, there is no need to do this. The EKAH theory is formulated for a wide frequency range. Instead of covering the whole frequency range, one can consider two extreme cases: the long-wave and short-wave frequency regions. The long-wave region is defined by the condition that the wavelength is much larger than the particle size.

The present invention is directed to particles smaller than 10 microns corresponding to the long-wave region. By adopting this restriction, significant simplifications of the mathematics and allows further generalization including particle—particle interaction.

From the users standpoint, there is a major advantage of employing this longwave restriction. The list of the required input parameters for characterizing the particles and liquid can be significantly shortened for many systems. In general, the ECAH theory requires knowledge of the density, heat capacity, heat conductance, and heat expansion for both the liquid and particles as well as the viscosity of the liquid. The required list is so long because both hydrodynamic and thermodynamic effects must be taken into account to describe the sound propagation through the dispersed system. However, the two effects are additive in the longwave region. This opens an opportunity to make further simplifications taking into account only the dominant effect. For instance, hydrodynamic effects are certainly dominant for rigid particles with sufficiently high density contrast. This includes a wide range of natural systems including oxides, minerals, pigments, paints, abrasives, ceramics, cement etc. Thermodynamic effects are negligible for acoustic characterization of these systems which then eliminates the necessity for knowing the thermodynamic properties for these systems. Acoustic characterization of these systems within the longwave region requires only knowledge of density and viscosity. The longwave restriction also makes it possible to use a sound speed theory in the concentrated system.

ELECTROACOUSTICS Background

There are two different approaches to electroacoustic measurements. The first approach employs an electric field to cause the particles to move relative to the liquid. This particle motion generates an ultrasound signal which can be measured. This approach is referred to as ElectroSonic Amplitude (ESA) approach. The ESA approach is more fully described in U.S. Pat. No. 4,497,208 No. 5,059,909 No. 5,245,290.

The second approach is the reverse of the first one: an ultrasound wave makes the particles move and a resultant electric signal is measured. The electric signal can be expressed as either a Colloid Vibration Potential (CVP) or Colloid Vibration Current (CVI) depending on whether one measures the open circuit voltage or the short circuit current between two suitable electrodes. The CVI mode is preferable because it eliminates the need to measure the complex conductivity in order to calculate the desired $\zeta$ potential. This approach is described in the U.S. Pat. Nos. 4,907,453, and 5,245,290.

The CVI mode is also more attractive because it allows one to simplify the hardware and perform measurement in the small volumes. This advantage of the CVI measurement is not used in the U.S. Pat. Nos. 4,497,208, 5,059,909, or 5,245,290 because these patents are devoted mostly to the ESA measurement. An instrument for exclusive CVI measurement can be simplified by using a special antenna which measures CVI locally but not across the whole sample.

Another important feature of the CVI measurement is the use of a pulse technique that distinguishes it from the art described in the U.S. Pat. No. 4,907,453 in which a continuos wave technique is described.

The Electroacoustic signal contains, in principle, information about both particle size and zeta potential. U.S. Pat. No. 5,059,909 suggests the use of such electroacoustic measurements at multiple frequencies for characterizing both parameters. However, there appears to be some penalty in trying to extract too much information from these electroacoustic measurements. Since both particle size and zeta potential are computed from the same set of data one would expect certain cross coupling in the sense that any error, for example, in the model relating to the electrokinetic properties would effect the calculated particle size. In addition, relying exclusively on the electroacoustic method would not provide any size information for uncharged particles or for particles in very high ionic strength media The largest problem with the Electroacoustics approach as compared to the Combined Spectroscopy approach is the lack of any electroacoustic theory which provides relationships between the electroacoustic signal and the PSD in a concentrated system. U.S. Pat. No. 4,497,208 No. 5,059,909 No. 5,245,290 claim to characterize PSD and $\zeta$ in a concentrated system but they give no theory which is valid above 5 volume %. There is no description or teaching in any of those patents of a means by which this claim can be substantiated.

A better approach to characterizing these two parameters is to use Combined Acoustic and Electroacoustic Spectroscopy in which acoustics is used for PSD characterization and Electroacoustics is used only for $\zeta$ potential. The present invention utilizes this combined approach in combination with other inventive features set forth below.

In contrast to the Electroacoustic approach which makes no claim to have suitable integrated theory for either particle size or zeta potential in concentrates, the current invention employs acoustic theory which is applicable for calculating particle size up to 50% by volume and a separate electroacoustic theory for calculating $\zeta$ potential in concentrates from CVI measurements.

SUMMARY OF THE INVENTION

This invention combines acoustic and electroacoustics spectrometers. These two spectrometers can be supplied as two more or less independent sensors combined in a single instrument.

The Acoustic sensor has identical transmitting and receiving piezoelectric transducers separated by a variable motor-controlled gap. The Electroacoustic sensor consists of a third piezoelectric transducer serving as transmitting transducer of ultrasound pulses and an electroacoustic antenna receiver separated by a fixed gap.

The combined sensor has a single piezoelectric transducer serving as both the transmitter and receiver of the ultrasound pulses and an electroacoustic antenna receiver separated by a variable motor controlled gap. The use of a single transducer for the acoustic measurement is made possible by using the reflected signal from the face of the antenna and measuring the round trip attenuation.

The Acoustic spectrometer measures the attenuation spectra using a pulse technique with variable gap between the transducers. It also measures the group sound speed at a selected frequency using time of flight measurement and adjusts the timing of the attenuation measurement for the actual sound speed in the sample. It also provides data of the phase sound speed by measuring the sound phase.

The measured sound speed is used to test the suitability of the model dispersion which is used as the basis for the calculation of both the particle size distribution and the $\zeta$-potential.

The Acoustic attenuation spectra is used for calculating the particle size distribution. Three different model distributions (monodisperse, modified lognormal and bimodal) are evaluated to test which one gives the best fit to the measured data. The theoretical attenuation is calculated using the attenuation theory and one of the model PSD distributions. The best fit is determined for each PSD model by searching for that PSD which minimizes the "error" between the theoretical attenuation and the experimental data. It is shown in this patent that different definitions of the "error" can provide certain performance improvements, particularly in difficult cases when the real world dispersion does not conform well to model dispersion used for developing the theory. The final PSD is then selected based on an evaluation of the fitting errors for all of the model distributions considered.

The Electroacoustic spectrometer measures the amplitude and phase of the Colloid Vibration Current at one or at multiple frequencies. The CVI at one frequency is used for calculating the $\zeta$-potential. The phase sound speed measured with the acoustic spectrometer is used to correcting the CVI phase, whereas the attenuation measured at this frequency provides correction for the CVI amplitude. The best particle size distribution calculated from the attenuation spectra is used for calculating the inertia effect and the effect particle—particle interactions.

Multiple frequency electroacoustic spectra is used for testing consistency between acoustic and electroacoustic measurements.

BRIEF DESCRIPTION OF THE DRAWINGS

FIG. 4. Titration $\zeta$-potential curves for rutile 7% vl and alumina 4% vl.

DETAILED DESCRIPTION OF THE INVENTION

The present invention is directed to a novel combination of Acoustic and Electroacoustic Spectroscopies. The present invention comprises various improvements in the hardware design, measurement techniques, prediction theory, and analysis. As is well known to those of ordinary skill in the art, the combination of Acoustic and Electroacoustic Spectroscopy provides a synergistic effect. One aspect of this synergy is the calculation of $\zeta$ potential from an Electroacoustic signal using the particle size calculated from the Acoustic attenuation spectra. The present invention is directed to other aspects of this synergy which apply to both the measurement itself as well as the analysis of the data.

Hardware Design

Figure 1:
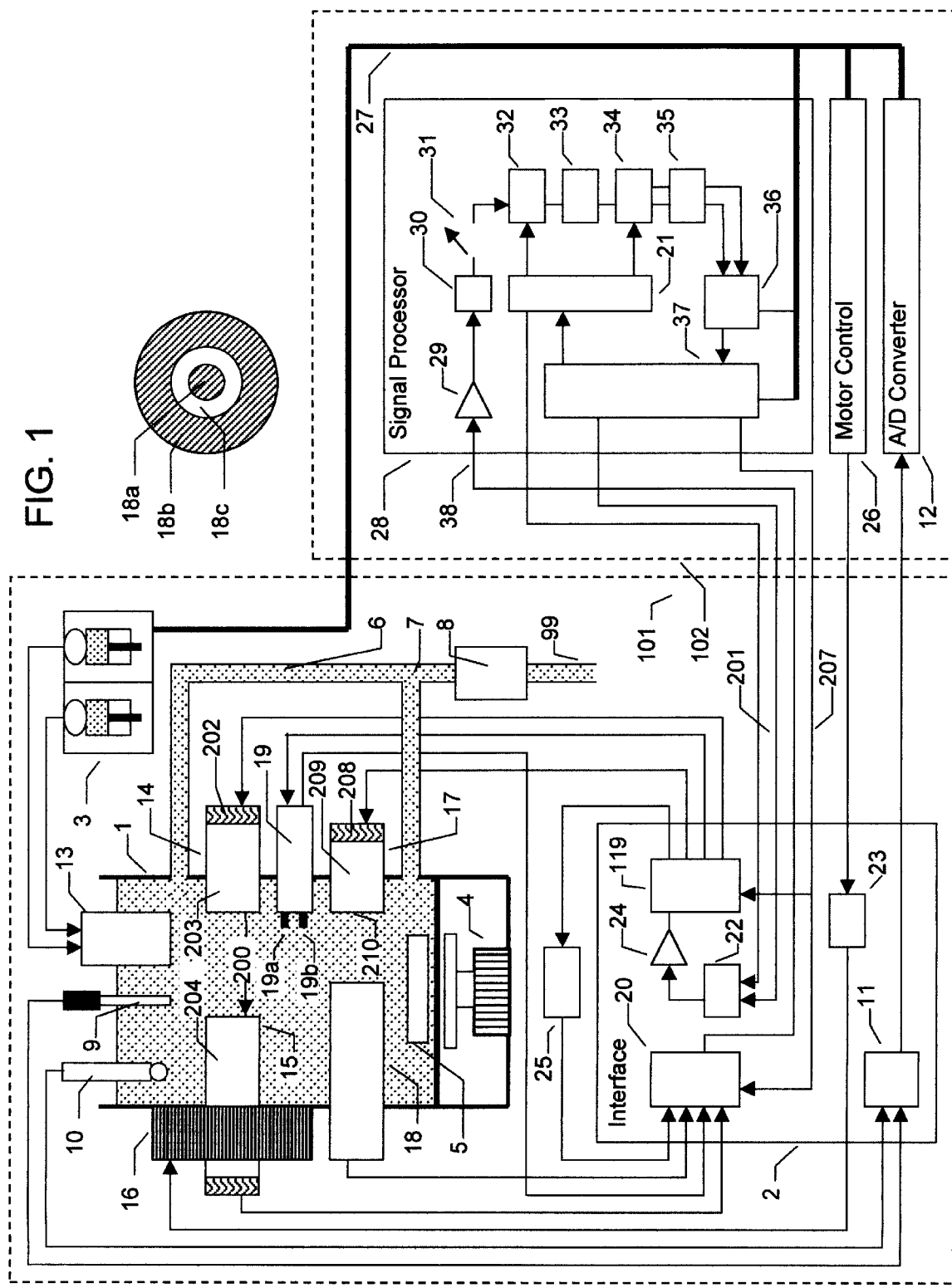
FIG. 1. Block diagram of two embodiments of the present invention.

The idea of synergism between Acoustic and Electroacoustic Spectroscopies is accomplished in the instruments known commercially as the Acoustic and Electroacoustic Spectrometer. There are commercially available models of these spectrometers. For example, Dispersion Technology, Inc. manufactures an acoustic sensor, model DT-1200 and a combined acoustic and electroacoustic sensor model DT-3000 respectively. FIG. 1 illustrates a block diagram of the two instruments.

As illustrated in FIG. 1, the overall system 100 is comprised of two units. The first is the measuring unit 101. The second is the electronics units 102.

The measuring unit 101 comprises a measuring chamber 1, interface electronics 2, and optionally a plurality of burettes 3. The burettes 3 are used for dispensing reagents into the measuring chamber 1. The burettes are connected to a dispensing probe 13 for the actual injection of the reagents into the test sample. A stirring motor 4 is magnetically coupled to a stir bar 5 that is located on the inside of the measuring chamber 1. When activated by the stirring motor 4, the stir bar 5 rotates and keeps the sample in the measuring chamber 1 mixed and aids in the distribution of the reagents added to the sample through the burettes 3. A bypass tube 6 fluidly connects the bottom and top of the measuring chamber 1. The centrifugal force created by the rotation of the stir bar 5 causes the sample to be pumped from the bottom to the top of the measuring chamber 1 through the bypass tube 6. The bypass tube 6 further comprises a tee fitting 7, a short piece of additional tubing 99 and a pinchclamp 8. The measuring chamber 1 can be drained through additional tubing 99 be opening the pinchclamp 8.

The measuring chamber 1 also comprises a conventional temperature probe 9 and pH probe 10. The temperature probe 9 and pH probe 10 are electrically connected to conventional electronics 11 and then to Analog/Digital coverter 12. In this way, the actual temperature and pH of the test sample is recorded. The measuring chamber 1 can also optionally be provided with sensors for measuring sound attenuation, Colloid Vibration Current (CVI), and the conductivity of the sample.

The acoustic attenuation sensor comprises a fixed transducer 14, a moveable transducer 15 and a stepping motor 16. The stepping motor 16 controls the moveable transducer 15. The CVI sensor comprises a fixed acoustic transmitting transducer 17 and a receiving antenna 18. The conductivity sensor 19 comprises two electrodes 19a and 19b for measuring electrical conductivity. Each of the sensors 14, 17 and 19 require an electrical excitation for proper operation. The excitation is provided by a dedicated channel of the output multiplexor 119. Likewise, each of the sensors 15, 18, and 19 generates an electrical signal that is routed to a dedicated channel of the input multiplexor 20.

A Measuring Unit Synthesizer 21 is also provided. The synthesizer 21 provides an RF signal that is converted by a gated mixer 22 to a source of pulsed RF by using timing waveforms supplied by the Field Programmable Gate Array FPGA 37. An RF power amplifier 24 is provided to amplify the RF signals to a level of 1 W. A reference channel 25 is also provided to allow for calibration of the unit.

The stepping motor 16 is driven by a motor drive 37. A conventional motor control board 26 controls the motor drive 23. The control board 26 is adapted to be received in a standard ISA computer bus 27.

A signal processor card 28 is also received in the computer bus 27. The signal processor card 28 comprises an input 38 that receives an output signal from the receiver 20. The signal processor card 28 further comprises an RF amplifier 29, a precise digital attenuator 30, a gated amplifier 31, a first mixer 32, an RF filter 33, a quadrature mixer 34, a high speed dual A/D converter 35, a Digital Signal Processor chip 36 for accumulating a large number of pulses and calculating necessary statistics, an FPGA 37 for generating the required gating signals, and a high speed dual synthesizer 21 for generating the RF signals required.

The device of the present invention contains independent acoustic and electroacoustic sensors. The acoustic sensor of the present invention is similar to the variable gap sensors known to those of ordinary skill in the art. It consists of the two pieso-electric transducers 14 & 15, exposed to the sample chamber from the opposite walls. The gap between face of the two transducers can be adjusted by means of the stepping motor 16 over a range from 0.15 to 20 millimeters. Commercially available Panametrics wide band transducers with a resonant frequency of 30 Mhz are typically used. The electroacoustic sensor consists of an acoustic transmitting transducer with a critical frequency 10 Mhz and an electroacoustic antenna 18.

The design of the electroacoustic antenna 18 is novel in several respects. The antenna 18 consists of two coaxial electrodes 18a and 18b separated with a non-conducting rigid ceramic insert 18c. Internal electric impedance between the two electrodes 18a and 18b can be selected by means of an internal transformer depending on the conductivity range of the sample in the measuring chamber 1. The transformer is selected such that the input impedance is significantly less than the external impedance of the sample. The resultant signal is, thus, proportional to the short circuit current. This transformer is located just behind the central electrode 18a in order to minimize any stray capacitance.

The construction method and geometry of this receiving transducer is novel and addressed several problems known in the art. For example, those of ordinary skill have experienced problem of an artifact in measuring colloid vibration potentials when either electrode is in contact with dissimilar material and at the same time exposed to the acoustic field. Such artifacts present difficulties particularly for samples having a low particle concentration or a low-density contrast. In the present invention, a potential source of such an artifact arises at the boundary between the inner electrode and the ceramic spacer and again at the interface between the outer electrode and this same spacer. The artifact is eliminated by the following two rules. One, the inner and outer electrodes 18a and 18b must be made from the exactly the same material and the surface chemistry of both surfaces must remain identical with time. Two, the sound field must be identical at both boundaries between the electrode and the insulating layer. By following these two rules, any artifact at one electrode boundary is canceled by the other.

One way to implement these rules is to make the annular spacer 18c quite thin. In this way, the outer diameter d1 of the inner electrode 18a is just slightly smaller than the inner diameter d2 of the outer electrode 18b. If the difference between d1 and d2 is small, the sound field will be almost the same at both boundaries. The question remains as to diameter d1 for the inner electrode 18a in relation to the sound intensity pattern of the transmitter. If the diameter d1 of the inner electrode 18a is much larger than the main lobe of the acoustic intensity, then the CVI signal generated at the middle of the central electrode 18a will be partially shunted by the portion of the electrode 18b which is not acoustically excited. The artifact is eliminated in this case because the sound intensity at these interfaces is zero. However, the desired CVI signal is unnecessary attenuated.

Conversely, if the central electrode 18a subtends only a small portion of the main lobe of the acoustic transmitter pattern, then only a small portion of the potential CVI signal is intercepted and the electrode boundaries receive a maximum acoustic energy so that any imbalance in the surface properties will result in an unwanted artifact. Clearly, the best geometry lies somewhere in between. In the present invention, it is preferred that a central electrode whose outer edge is located at 30% point on the acoustic intensity pattern is a reasonable operating point, although this may not be quite optimum. In addition, it is preferred that inner and outer electrodes 18a and 18b be constructed from 316 stainless steel providing that both the inner and outer electrodes 18a and 18b are made from the same piece of the raw material. It is anticipated that gold will perform better than 316 stainless steel but has not been used. The ceramic spacer 18c is made from a polyamide resin such as Vespel which is manufactured by DuPont. The pieces are press fit together using cyanoacrylic cement as a sealant and then optically polished. The quality of the final product is tested by measuring the background signal in 0.01 M KCl. Ideally the signal in KCl should be zero since the ion vibration signal for this particular pair of ions is essentially zero.

The transmitting transducer 17 and the receiving antenna 18 are mounted in the opposite walls of the measuring chamber 1. In the configuration of the present embodiment, the gap between the faces is 5 millimeters.

The design of the present invention provides great flexibility for the user since the acoustic sensor and the electroacoustic sensor can be used either individually or in conjunction with the other. If both are used in conjunction, a sample of approximately 100 ml is required. If only one of the two sensors are used, the sample volume can be reduced to as little as 30 ml. This sample volume is much less than is required for prior instruments.

An alternative embodiment of the present invention is to combine the Acoustic and Electroacoustic sensors together in one hardware block. This sensor block is somewhat similar to the acoustic sensor described above except that an electroacoustic antenna 18 replaces the acoustic receiver 15. The gap between transducer and antenna is adjusted by means of the stepping motor 16. The combined sensor can measure both acoustic and electroacoustic parameters using only one instead of three sound transducers. Operation of this combined sensor is more complicated because the single sound transducer must perform the functions of both transmitter and receiver.

The electronics of both of the above described instruments consists of two special purpose boards: the Signal Processor and Interface. The Signal Processor board is adapted for plug-in use in a personal computer which using Windows-95 based software for the user interface. The personal computer further comprises a conventional Data Acquisition card, a motor control card and display adapter card for the monitor.

Measurement Technique

The operating program of the acoustic sensor of the present invention is quite different than available acoustic sensors. The instrument of the present invention is directed to creating synergy between the attenuation and sound speed measurement. Errors in sound speed lead to errors in the attenuation measurement because the received pulse is sampled at the wrong moment in time. This causes excess attenuation especially at the low end of the frequency range.

Attenuation data is also necessary for accurate sound speed measurement in concentrated systems. In concentrated systems, the sound speed can only be measured for certain gaps for which the attenuation is not so high as to preclude adequate signal to noise ratio The acoustic sensor of the present invention measures both sound speed and attenuation at multiple frequencies using pulse techniques.

The acoustic sensor measurements are made using a defined grid consisting of a number of frequencies and a number of gaps. Typically 18 frequencies are selected between 1 and 100 MHz in logarithmic steps and 21 gaps between 0.15 to 20 mm also in logarithmic steps. These conditions may be modified automatically by the program depending on apriori knowledge of the sample or manually by one of ordinary skill in the art.

The FPGA 37 generates the transmit gate which, in turn, defines a 1 Watt pulse generated in the Interface module. In addition, the signals necessary to set the frequency to any point on the grid are also generated. At the beginning of the each measurement, a transmit multiplexor 119 routes the pulses to a fixed 40 dB reference attenuator 25 and similarly, the receiver multiplexer 20 routes the output of this attenuator to the input 38 of the signal processor. Since the precision attenuator has a known response over the entire frequency range, this step allows other losses to be characterized in the measuring circuits at each frequency.

The next step in the measurement is to determine the losses in the acoustic sensor 14 for each point on the measurement grid. The FPGA 37 commands the transmit and received multiplexors 119 & 20 via control signals to substitute the acoustic sensor 206 for the reference attenuator 25. The 1 watt pulses are sent to the transmitting transducer 14 where a piezoelectric crystal 202 converts these electric pulses to sound pulses. The sound pulses propagate through the quartz delay rods 203, pass through the gap 200 between the transducers 14 & 15 which is filled with the dispersion under test, enter an identical quartz rod 204 associated with the receiving transducer 15, are converted back to an electrical signal in the receiving transducer 15 and finally are routed through the receiving multiplexor 20 to the input signal port 38 on the Signal Processor 28 where the signal level of the acoustic sensor output is measured. For each point on the grid, the DSP 36 collect data on a minimum of 800 pulses but the number of pulses which are collected will automatically increase as necessary to obtain a target signal to noise ratio. Typically the target is set for a signal to noise ratio of 40 dB which means that the received signal power will be 10,000 times the noise power. This is usually more than sufficient to insure quality acoustic spectra. Those of ordinary skill in the art can tailor the measurement parameters to provide the proper trade-offs between measuring speed and precision.

Comparison of the amplitude and phase of the acoustic sensor output pulse with that of the reference channel output pulse allows the program to calculate precisely the overall loss in the acoustic sensor at each frequency and gap 200.

The acoustic sensor loss nominally increases linearly with the gap 200. A regression of the acoustic sensor loss with gap yields the attenuation of the dispersion in terms of dB/cm. Since in general the attenuation for most materials, even water, increases strongly with frequency, it is conventional to divide the above attenuation by frequency in MHz so that the final output is expressed in dB/cm*Mhz.

The above regression analysis provides not only the slope of the sensor loss from which we compute attenuation, but also an intercept corresponding to the sensor loss at zero gap. Since the loss in the sample by definition is zero for zero gap, this intercept provides a measure of all other losses in the acoustic sensor. These losses are lumped together and referred to as the "transducer loss" and include the loss in converting the electrical pulse to acoustic energy in the transmitting transducer 14, reflection losses at various interfaces, and the loss in converting the acoustic energy received by the receiving transducer 15 back to an electrical signal. Although the transducer losses are not necessary for the calculation of the attenuation, it provides a good integrity check on the system performance and allows any degradation in the sensors to be detected long before any loss in system performance is measurable.

The number of pulses collected for each frequency and gap on this grid is automatically adjusted to obtain a target signal-to-noise ratio. The RF pulse processed in the Signal Processor 28 exhibits a bell shaped response. For maximum accuracy the amplitude must be measured at the peak of this curve. For small gaps, A/D 35 samples the pulses at a moment calculated using the theoretical sound speed. For larger gaps an optimum pulse arrival time is determined for at least one selected frequency by making a few additional measurements at time intervals slightly shorter and longer than the nominal value. The optimum time of arrival is computed by fitting a polynomial curve to the few points measured on this bell shaped response. This procedure typically provides a precision of a few nanoseconds in the computation of the optimum arrival time. The measured error in arrival time for this frequency and gap is accumulated with each increasing gap. For each subsequent point on the grid, the signal is sampled at a time interval which is the sum of the time calculated from the theoretical sound speed and the last updated value for the cumulative error in arrival time A regression analysis of the optimum arrival time with gap provides an accurate measure of the group sound speed. This procedure of the time of flight adjustment achieves two goals. First, it eliminates the possible artifact in attenuation measurement, second, it provides the group sound speed measurement. This sound speed measurement is much more reliable than for one fixed gap because it is made at several gaps with averaging. Attenuation of sound makes measurement of the time of flight less accurate at the larger gaps where intensity of the arriving signal is low. In order to improve the sound speed measurement program selects only those gaps where attenuation of sound is still sufficiently low. This method makes possible to measure group sound speed at much wider dynamic range comparing to the fixed gap technique.

Sound speed measurement is even more important in an embodiment where a single transducer must perform both functions of transmitter and receiver. Information of the sound speed or the time of flight must be very accurate in order to switch transducer functions. Acoustic measurement is almost identical for this instrument because the arriving pulse is a reflection of the transmitted pulse from the surface of electroacoustic antenna. Consequently, the time of flight is twice longer in this case. An appropriate correction for acoustic impedance is required when the balance of the acoustic energy is calculated.

Sound speed data is also required for electroacoustic measurement. However, it is the phase sound speed which is required in this case. Thus, in addition to the described time of flight measurement, the phase of the acoustic signal is measured as well. The phase of the acoustic signal provides information for determining the phase sound speed that is, in turn, used further for correcting CVI phase.

Electroacoustic measurement can be done with either fixed gap or variable gap embodiments described above. In contrast with acoustic measurement, variable gap provides no advantage for electroacoustic measurement. In any event, electroacoustic measurement requires calibration of the instrument with the known colloid.

Electroacoustic measurement can be performed either for one frequency or for the chosen set of frequencies from 1 to 100 MHz. One frequency measurement is sufficient for calculating ζ potential if particle size and sound attenuation are both known. Multiple frequency measurement is used for various consistency tests as described below.

The electroacoustic measurement is similar to the acoustic measurement. The Signal processor 28 generates electric pulses of the certain frequency and length. A piezoelectric crystal 208 in acoustic transducer 17 converts these pulses to the sound pulses with some certain efficiency. The value of this efficiency is not important in this case because the absolute acoustic power in the sample is calibrated with the known colloid.

A sound pulse will then propagate through the quartz delay rod 209 and partially reflects from the delay rod surface 210 which is contacting the sample. The other part of the pulse propagates through the sample. The portion of the acoustic energy which is lost in the reflected part of the pulse can be calculated using ration of the acoustic impedance of the delay rod 209 and of the sample. The acoustic impedance of the sample is determined by the sound speed. That is the first sound speed correction during electroacoustic measurement.

An acoustic pulse propagating through the sample excites particles and disturbs their double layers. The particles will gain dipole moments because of this excitation. These dipole moments generate electric field. This electric field changes the electric potential of the central electrode 18a of the electroacoustic antenna 18. The difference of the electric potentials between central electrode 18a and external reference electrode 18b will cause electric current. This current is registered as Colloid Vibration Current.

The value of this current is very weak and requires averaging of over at least 800 pulses in order to achieve in appropriately high signal to noise ratio. The number of pulses depends on the properties of colloid. The measurement of CVI in low conducting oil based systems requires averaging of millions pulses. In principle, this method makes it possible to measure any low energy signals.

Both the magnitude and phase of the Colloid Vibration Current are necessary for the complete ζ potential characterization. The phase measurement requires again information of the phase sound speed. This is another point of the synergism between acoustic and electroacoustic measurements.

Electroacoustic measurement performed with variable gap as described herein provides another advantage. This method provides an independent test of the acoustic and electroacoustic measurement consistency. The electroacoustic signal will decay with increasing gap because of the sound attenuation. It means that measurement of CVI versus gap for the set of frequencies gives independent information about sound attenuation coefficient. This electroacousticaly measured attenuation coefficient can be compared with attenuation measured with acoustic sensor. Correlation between these two attenuation spectra is a measure of the consistency between acoustic and electroacoustic measurements.

Prediction Theory

As it is known to those skill in the art, Combined Acoustic and Electroacoustic Spectroscopy, the attenuation spectra provides information for the particle size calculation, whereas the CVI measurement provides the data for the ζ potential calculation. The first step in these calculations is the development of an adequate and realistic model for describing the real dispersed system. The presently available model assumes the system can be described as an assembly of separate spherical homogeneous particles in a Newtonian media. In this model "separate" means that there is no structure connecting particles. The spherical assumption is reasonable because particles with an aspect of as much as 5:1 seem to fit the model quite adequately. Homogeneous refers to the assumption that each particle has the same properties from the surface to the center.

Generally, the following set of physical-chemical material properties for both the particles as well as the liquid must be known: the density (ρ), viscosity (η), sound speed (c), intrinsic attenuation ($\alpha_{int}$), thermal expansion (β), thermal conductance (k), thermal capacity ($c_p$) must be known. Depending on the values of some properties, the values of others may not required in some cases.

There are no objective criteria for automatically determining the adequacy of the model known to those of ordinary skill in the art. It is clear that such a test is very important. A mistaken choice of the model system can cause enormous errors in the particle size and zeta potential. The test of the model is especially important for concentrated systems which are often structured. The test should be independent of the particle size and zeta potential. The present invention is directed to using the deviation between the measured and predicted sound speed as an objective criteria to determine the accuracy of the model. In concentrated systems, the sound speed is not constant but is a function of frequency. The sound speed asymptotically approaches a low frequency (relaxed) limit and a high frequency (frozen) limit. These asymptotic sound speeds are independent of the particle size, they depend only on the material properties of the particles and the media and the volume fraction.

The general theory of the so-called equilibrium sound speed has recently been developed prior to the present invention. Accordingly, the low frequency relaxed sound speed equals $$\frac{c_{sf}^2}{c_s^2(0)} = \gamma_f \frac{1-\phi_v}{1-\phi_m}\left(1 - \phi_v + \phi_v \frac{\rho_f c_{sf}^2/\gamma_f}{\rho_p c_{sp}^2/\gamma_p}\right) - (\gamma_f - 1)\frac{(1-\phi_v + \phi_v \beta_p/\beta_f)^2}{1+\phi_m(c_{pp}/c_{pf}-1)} \quad (1)$$

where indexes f and p correspond to the fluid and particle, γ is a specific heat ratio, $\phi_v$ is a volume fraction, $C_m$ is a mass loading, $\phi_m = C_m/(1+C_m)$.

Equation (1) results in the relaxed sound speed for elastic particles. In the case of the rigid solid particles Equation (1) can be simplified because the specific heat ratio of the liquids is very close to 1. By incorporating this simplification, the so-called Wood sound speed results as follows:

$$\frac{c_{sf}^2}{c_s^2(0)} = (1-\phi_v)^2(1+C_m) \quad (2)$$

Figure 2:
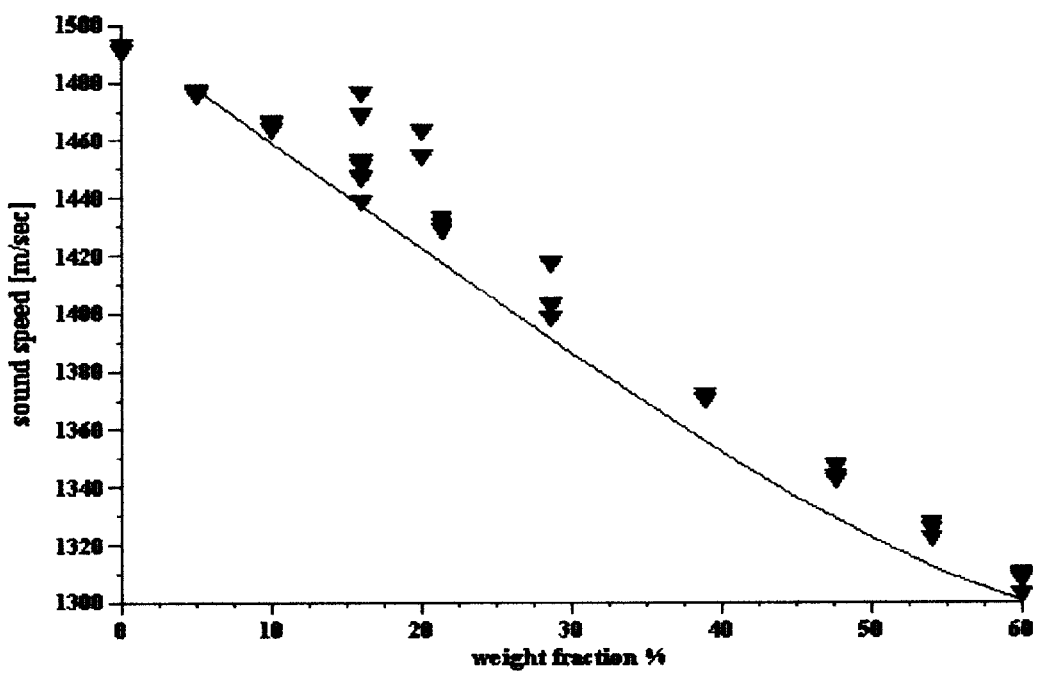
FIG. 2. Sound speed measured for alumina AKP-30 for versus weight fraction and calculated following Wood equation (2).

According to this expression the low frequency sound speed of a dispersion of rigid particles depends only on the density and weight fraction. As illustrated in FIG. 2, a dilution experiment performed with alumina AKP-30 confirms the validity of Wood expression for rigid particles.

A deviation in the measured low or high frequency sound speed from the corresponding calculated value is an indication that the model may not be adequate to describe the dispersed system due to one of the following reasons: (I) either the assumption of the dispersed particles being separate is not valid, (II) or that the stated properties of the disperse phase or media are incorrect.

The estimated particle size distribution is calculated according to methods known to those of ordinary skill in the art.

There are several methods to check the consistency of the calculated particle size. One method is related to sound speed. According to this method, one can calculate sound speed for the given particle size distribution at any frequency and volume fraction for dispersions with high density contrast, like ceramics, oxides, pigments etc. This theoretical sound speed can be compared with experimentally measured phase sound speed.

Another consistency test is based on the general relationship between group sound speed and phase sound speed as follows:

$$c_g = c_{ph}\left(1 - \frac{f}{c_{ph}}\frac{dc}{df}\right)^{-1} \quad (3)$$

where: $c_g$ and $c_{ph}$ are group and phase sound speed correspondingly, f is a frequency, derivative is taken at the frequency of measurement.

The sound speed derivative in the Equation (3) can be calculated using theoretical values for the sound speed for the best particle size distribution. Substitution of this theoretically calculated derivative into the Equation (3) must reconcile experimental values of the group sound speed and phase sound speed.

Calculation of the ζ-potential from the measured CVI value requires theory describing electroacoustic phenomena in concentrated dispersed system. This theory must take into account particle—particle interaction as well as interaction of the particles with the solid surface of the electroacoustic antenna. One such theory takes into account particle—particle interaction as well as inertia related effects using cell model. We use a simplified version of the cell model theory which is valid for large χa ($\chi^{-1}$ is a double layer thickness) and a low surface conductivity.

Electroacoustic theory must take into account interaction of the particles with antenna surface in addition to the particle—particle interaction. This interaction is referred to as the backflow effect. In the case of the constant electric field corresponding to the microelectrophoresis this effect brings multiplier $(1-\phi_v)$ into the equation for electrophoretic mobility.

Analysis for Combined Spectroscopy

An Analysis Engine is essentially a set of algorithms implemented in a computer program which calculates the desired characteristics from the measured data using the knowledge contained in the prediction theory. The analysis can be thought of as the opposite or inverse of prediction. Prediction describes some of the measured properties in terms of the model dispersion. The analysis, given only the values for some of the model parameters, attempts to calculate some of the remaining properties by an analysis of the measured data.

In general the calculation of the particle size distribution or the zeta potential is performed by adjusting the estimate of the particle size parameters or the zeta potential until the error between the values of the measured properties and those same properties calculated from the prediction theory using this estimate is minimized. The adjustments may be global, that is over the whole range for which the instrument is designed, or local about some preset value.

This calculation is a combination of the global and local searches with particle size distributions with pre-defined shape. The three different distributions are tested in turn: monodisperse, lognormal and bimodal. The search for the best monodisperse PSD is global, in the sense that particles sizes from 10 nm to 30 microns are tested with a certain logarithmic step. The best monodisperse solution is used as a starting point for the lognormal search. This search is initially global for PSD standard deviation with further local adjustment.

In the general case there are two local minimums of the error function for the lognormal PSD. This is because the attenuation spectra of very large particles is quite similar to that for very small particles. The viscous losses component for the small particles appears quite similar to the scattering loss for large particles. For this reason, a global search for the best solution is very important. The best lognormal PSD is used as initial starting point for a bimodal search.

The reliability of the particle size distribution is characterized with errors of theoretical fit to experimentally measured attenuation spectra. This error analysis makes it possible to chose the most probable PSD.

Figure 3:
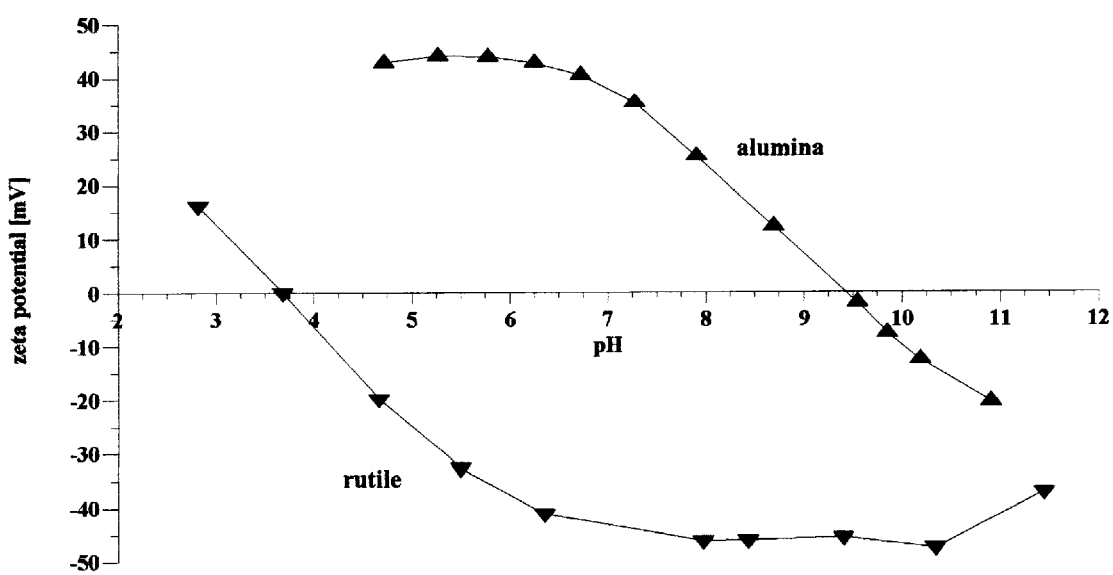
FIG. 3. Errors of theoretical fitting attenuation spectra measured for rutile 7% vl and alumina 4% vl achieved with lognormal and bimodal distributions for the different pH.

Error analysis is especially important for characterizing non-stable systems. FIG. 4 shows theoretical fit errors for alumina (4% vl) and rutile (7% vl) dispersions for various pH. Corresponding ζ-potential titration curves are shown on FIG. 3. These fitting errors indicate that lognormal PSD fails to fit experiment near isoelectric point. The bimodal PSD analysis properly characterizes the aggregation phenomena near the isoelectric point.

The best particle size distribution as well as measured attenuation and sound speed are used for calculating ζ-potential from CVI. A sound pulse will attenuate as it propagates through the sample towards antenna 18 where it generates the measured CVI. The value of CVI is proportional to the sound intensity near the antenna 18. This value of the sound intensity at the CVI sensor is different than the initial sound intensity due to the attenuation of the pulse. The attenuation determined from the acoustic sensor is used to make this intensity correction in the CVI measurement.

This sound speed correction is important for correcting the phase of the CVI. The result of this correction is the phase sound speed. The phase sound speed is either measured independently or calculated from the group sound speed using the best particle size distribution. The required accuracy of the CVI phase measurement is not as rigorous in comparison to other methods known in the art as are described in U.S. Pat. Nos. 5,245,290 and 5,059,909. This phase information is used only for determining the sign of ζ-potential, while in these prior art methods it is used as a source of PSD data.

As is known to those of ordinary skill in the art, the conventional rule relating CVI phase with the sign of ζ is as follows. A particle is negatively charged (ζ<0) if CVI phase is more than 90° and less than 270°. For other phases, the particle is positively charged (ζ>0).

The allowed error in the CVI phase measurement is about 90°. However, in the many cases, the error can exceed 90° if sound speed is wrong. Accurate measurement of the sound speed with an acoustic sensor is essential for correct determining the sign of the particles charge.

The last step of calculations is a test of consistency between acoustic and electroacoustic measurements. Particle size known from acoustics and ζ-potential known from the single frequency electroacoustic measurement makes it possible to calculate the multifrequency electroacoustic spectra. Comparison of this theoretical electroacoustic spectra with experimentally measured one is a criterion of the consistency. The match between theory and experiment indicates consistent and reliable particles characterization.

Precision and Accuracy

As used herein, precision is a measure of the reproducibility of output from the sensors for a given sample. This section presents results concerning precision of the both Acoustic and Electroacoustic sensors.

Figure 5:
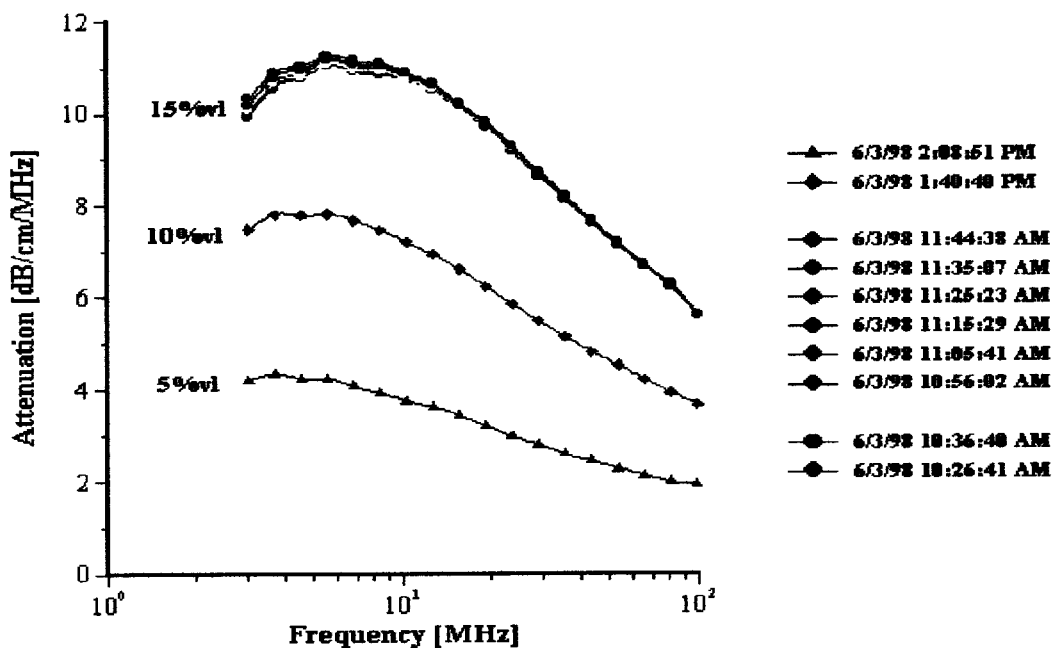
FIG. 5. Attenuation spectra measured for alumina Sumitomo AKP-15 at volume fractions 5% vl, 10% vl and 15% vl. Measurement at 15% vl was repeated 10 times.

This reproducibility test was made with alumina Sumitomo AKP15 at pH=4 and volume fraction 15%. Measurement was repeated 10 times. FIG. 5 illustrates attenuation spectra corresponding to the measurements. Colloid Vibration Current was measured together with attenuation. The corresponding median particle size, standard deviation and zeta potential are shown in Table 1.

As illustrated in Table 1, the variation of the median particle size is 0.4% whereas variation of the $\zeta$-potential is 1%. This numbers illustrate precision of the Acoustic and Electroacoustic sensors in the present invention.

As used herein, accuracy is a measure of the correlation between real and measured values. The accuracy of the PSD measurement is a measure of adequacy of the measured particle size distribution. In order to determine accuracy of the PSD measurement, a standard system with a known particle size distribution is required. The present invention utilizes a BCR Silica quartz with the median size about 3 microns. The BCR silica quartz is the German PSD standard.

Figure 6:
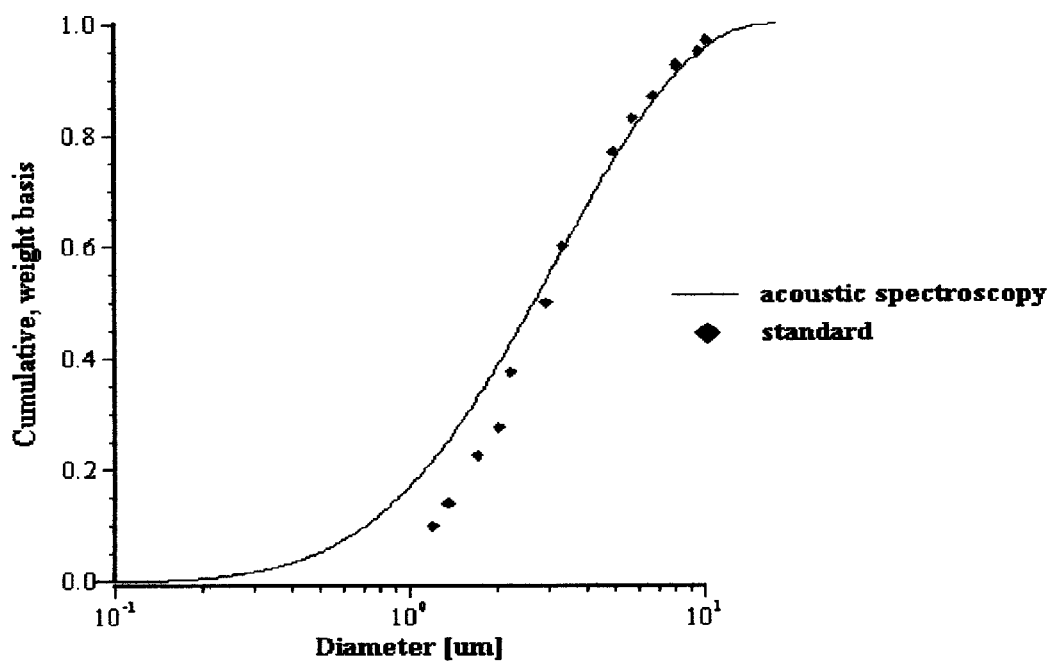
FIG. 6. Particle size distributions standard and measured acoustically for silica quartz BCR at 11 % wt in ethanol.

FIG. 6 illustrates the standard particle size distribution and PSD measured with the acoustic sensor of the present invention. The difference of the median particle size between the BCR silica quartz standard and acoustic sensor of the present invention is less than 1%. However, there is some difference in the number of small particles. Consequently, the Acoustic sensor determines median size with an accuracy 1% and standard deviation with an accuracy of about 5%.

Test of the $\zeta$-potential measurement accuracy is much more complicated because there is no $\zeta$-potential standard for concentrated systems. Absence of the electroacoustic theory for concentrated systems creates additional complexity. Our experience is that CVI makes it possible to measure $\zeta$ with the almost same accuracy as microelectrophoresis.

Those of ordinary skill in the art will recognize that the embodiments just described merely illustrate the principles of the present invention. Many modifications may be made thereto without departing from the spirit and scope of the invention as set forth in the following claims,

TABLE 1

Reproducibility test measurement with alumina AKP-15, 15% by volume in KCl 0.001 mol/l with pH = 4.

| Median size [micron] | Lognormal PSD Standard Deviation | $\zeta$ [mV] | Measurement date |
|---|---|---|---|
| 0.6362 | 0.2 | 47.04 | "6/3/98 11:54:22 AM" |
| 0.6354 | 0.2 | 47.6 | "6/3/98 11:44:38 AM" |
| 0.6332 | 0.21 | 46.36 | "6/3/98 11:35:07 AM" |
| 0.6332 | 0.2 | 46.2 | "6/3/98 11:25:23 AM" |
| 0.6364 | 0.195 | 46.94 | "6/3/98 11:15:29 AM" |
| 0.6272 | 0.21 | 45.51 | "6/3/98 11:05:41 AM" |
| 0.6335 | 0.2 | 46.7 | "6/3/98 10:56:02 AM" |
| 0.6311 | 0.21 | 45.86 | "6/3/98 10:46:23 AM" |

TABLE 1-continued

Reproducibility test measurement with alumina AKP-15, 15% by volume in KCl 0.001 mol/l with pH = 4.

| Median size [micron] | Lognormal PSD Standard Deviation | $\zeta$ [mV] | Measurement date |
|---|---|---|---|
| 0.6282 | 0.2 | 46.2 | "6/3/98 10:36:40 AM" |
| 0.6303 | 0.195 | 46.72 | "6/3/98 10:26:41 AM" |

What is claimed is:

1. A method for characterizing particle size distribution and $\zeta$-potential using measurement of sound attenuation frequency spectra, sound-speed, magnitude and phase of a Colloid Vibration Current in pure liquids or dispersed systems comprising a sound transmitter and a receiver wherein there is employed one or more gaps between transmitter and receiver and such method comprises the steps of the sound transmitter generating a sound pulse of certain variable frequency that will propagate through a test sample, interacting with it and then being measured by said receiver and compared with the initial pulse for characterizing energy loss which depends on the particle size and/or the $\zeta$-potential depending on the type of the receiver.

2. A method for measuring sound attenuation frequency spectra and sound-speed in pure liquids or dispersed systems wherein the receiver of claim 1 is an acoustic receiver measuring intensity and phase of the sound pulse.

3. A method for measuring the magnitude and phase of the Colloid Vibration Current in dispersed systems wherein the receiver of claim 1 is an electroacoustic antenna comprising two coaxial electrodes measuring current generated by the sound pulse.

4. The method of claim 2 wherein the number of pulses collected is automatically adjusted to obtain a target signal to noise ratio.

5. The method of claim 2 wherein an uncertainty in the pulse arrival time corresponding to an uncertainty in an a priori sound speed is removed by the additional step of making additional measurements at time delays shorter and longer than an expected time delay.

6. The method of claim 5 comprising the further step of performing a linear regression analysis of an optimal pulse arrival time versus said gaps is used to compute a group sound speed for the test sample.

7. The method of claim 5 comprising the further step of calculating the attenuation spectra of the test sample by linear regression analysis of the acoustic loss versus said gaps for a set of said variable frequencies.

8. The method of claim 6 comprising the further step of calculating the particle size distribution fitting the experimental attenuation spectra with theoretically calculated spectra using a "coupled phase model" and "cell model".

9. The method of claim 7 comprising the further step of testing the accuracy of the particle size distribution calculated from the measured attenuation spectra by comparing an experimental sound speed with theoretical sound speed.

10. The method of claim 1 comprising the further step of calculating the $\zeta$-potential and fitting the experimental Colloid Vibration Current spectra with theoretically calculated spectra using a "coupled phase model" and "cell model".

11. The method of claim 6 comprising the further step of calculating the volume fraction of the dispersion by fitting the experimental sound speed with the theoretically calculated sound speed using a "coupled phase model" and "cell model".

* * * * *